United States Patent [19]

Bach

[11] Patent Number: 4,861,163

[45] Date of Patent: Aug. 29, 1989

[54] ELLIPSOIDAL CYLINDER FLUORESCENCE ANALYZER

[75] Inventor: David T. Bach, Westborough, Mass.

[73] Assignee: Amoco Corporation, Chicago, Ill.

[21] Appl. No.: 141,160

[22] Filed: Jan. 6, 1988

[51] Int. Cl.$^4$ .............................................. G01N 21/64
[52] U.S. Cl. .................................. 356/417; 250/458.1
[58] Field of Search ....................... 356/317, 318, 417; 280/458.1, 459.1, 461.1, 461.2

[56] References Cited

U.S. PATENT DOCUMENTS

| | | |
|---|---|---|
| 3,455,622 | 7/1969 | Cooper . |
| 3,788,744 | 1/1974 | Friedman et al. ..................... 356/39 |
| 3,946,239 | 3/1976 | Salzman et al. ........................ 356/39 |
| 4,002,896 | 1/1977 | Davies et al. . |
| 4,049,970 | 9/1977 | Ford ................... 250/461.2 |
| 4,188,542 | 2/1980 | Hogg et al. ........................ 250/373 |
| 4,188,543 | 2/1980 | Brunsting et al. ............... 250/458.1 |
| 4,189,236 | 2/1980 | Hogg et al. ........................ 356/317 |
| 4,208,587 | 6/1980 | Eastlund et al. ..................... 356/372 |
| 4,672,169 | 6/1987 | Chambers ........................ 219/121 L |
| 4,744,667 | 5/1988 | Fay et al. ............................. 356/417 |

FOREIGN PATENT DOCUMENTS 3507171 9/1986 Fed. Rep. of Germany ... 250/458.1

OTHER PUBLICATIONS

*Farrand Ratio Fluorometer* (brochure), May 1968.
Mroz, E. A. and Lechene, C., "Fluorescence Analysis of Picoliter Samples", Analytical Biochemistry 102, 90–96 (1980).

Primary Examiner—F. L. Evans
Attorney, Agent, or Firm—Bruce A. Walker; William H. Magidson; Ralph H. Medhurst

[57] ABSTRACT

The present invention provides an apparatus and method for fluorescence detection. An ellipsoidal cylinder having a first focal line, a second focal line and an internal reflective surface is provided. An excitation source is disposed on the first focal line and a sample container is disposed on the second focal line. Filter means are disposed between the excitation source and the sample container. Both fluorescence detector and reference detector means are provided to detect, respectively, the fluorescence radiation and excitation radiation. Comparator means compare the signal from the fluorescence and reference detectors to determine the presence and concentration of fluorescent material within the sample container.

22 Claims, 4 Drawing Sheets

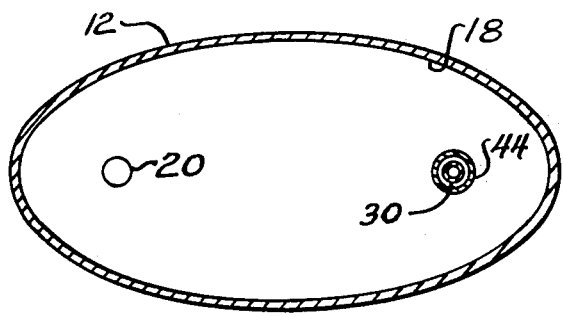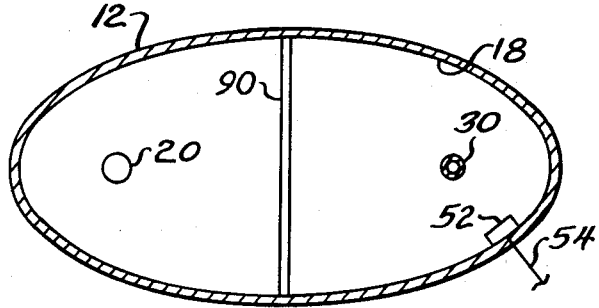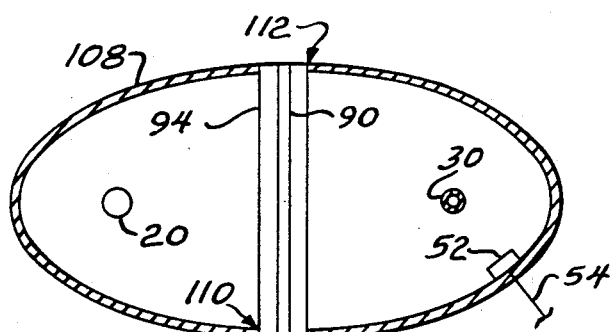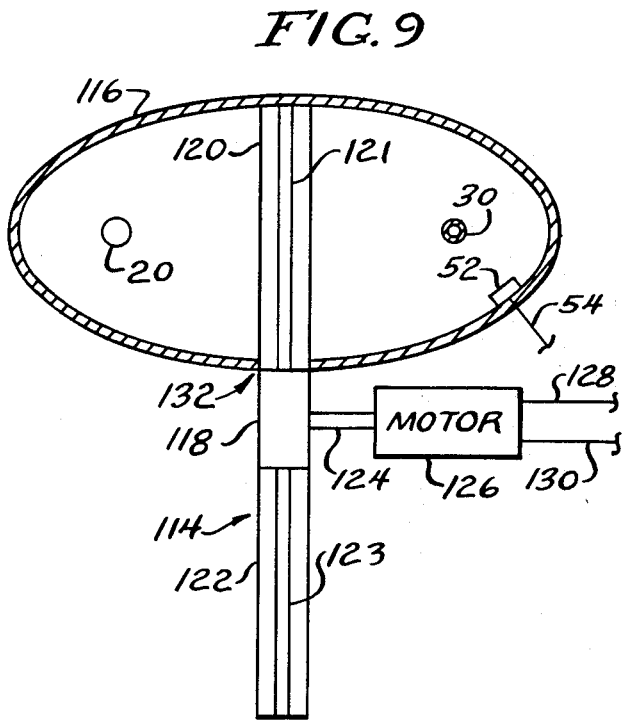

ELLIPSOIDAL CYLINDER FLUORESCENCE ANALYZER

BACKGROUND OF THE INVENTION

The present invention relates to fluorescence analyzers and, more particularly, to flourescence detectors wherein the excitation radiation emanates from one focal line of an ellipsoidal cylinder and the sample is located at the other focal line.

As discussed in "Fluorescence Analysis of Picoliter Samples", Edmond A. Mroz and Claude Lechene, Analytical Biochemistry 102, 90–96 (1980), biochemical analysis of very small samples—on the order of picoliters—is required in both basic and applied sciences of cell biology. As explained, many attempts to analyze such samples have been tried, and many of these attempts have used microfluorescence methods. These methods have limitations, however, in the compounds that can be analyzed and the ease with which assays can be performed. The apparatus disclosed in the above-referenced article is a fluorometer chamber, created optically by using a capillary tube as a flow cell and a microscope-fluorometer to excite fluorescence in and to record fluorescence from a constant region within the capillary. Excitation radiation is directed transverse to the capillary tube and fluorescent radiation is similarly collected transverse to the capillary tube.

Such an apparatus has inherent problems in that the exitation radiation is not efficiently delivered to the sample volume because it is directed transverse to the capillary tube and, consequently, passes through only a small portion of the sample volume in the capillary tube. Further, the fluorescent radiation cannot be efficiently collected and delivered to a detector. The cumulative loss of excitation and fluorescent radiation results in an instrument having greatly reduced sensitivity.

SUMMARY OF THE INVENTION

It is an object of the present invention to provide a fluorescence analyzer capable of measuring the concentration of fluorescence samples.

It is a further object of the invention to provide such a fluorescence analyzer wherein the excitation radiation is efficiently delivered to the sample and the fluorescence radiation from the sample is efficiently collected and detected.

It is a further object to provide a fluorescence analyzer wherein that portion of the detector holding the sample can be made compact and inexpensive.

It is a still further object to provide a fluorescence analyzer wherein a variety of selectable excitation frequencies can be employed.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the ellipsoidal cylinder fluoresence analyzer for analyzing a sample of this invention comprises an ellipsoidal cylinder having a first focal line, a second focal line and an internal reflective surface, a radiation source disposed substantially along the first focal line; a container suitable for containing the sample disposed between the radiation source and the sample container for passing a selected portion of the electromagnetic spectrum; fluorescence detector means for detecting fluorescent radiation emanating from the sample container and generating a signal in response thereto, and, preferably, in proportion thereto; reference detector means to detect radiation that has passed through the filter means and generating a signal in response thereto, and, preferably, in proportion thereto; and comparator means for comparing the signals from the fluoresence and reference detectors and generating a signal indicative of the presence and concentration of fluorescent substances in the sample.

The accompanying drawings, which are incorporated in and constitute a part of this specification, illustrate one embodiment of the invention, and, together with, the description, serve to explain the principles of the invention.

BRIEF DESCRIPTION OF THE DRAWINGS

FIG. 2 is a sectional schematic diagram taken along line II—II of FIG. 1 of an ellipsoidal cylinder fluorescence analyzer in accordance with the present invention;

FIG. 7 is a sectional view of an ellipsoidal cylinder having a medial filter in accordance with the present invention;

FIG. 8 is a sectional view of an ellipsoidal cylinder having a reciprocating selectable medial filter in accordance with the present invention;

FIG. 9 is a sectional view of an ellipsoidal cylinder having a rotating selectable medial filter in accordance with the present invention.

DESCRIPTION OF THE PREFERRED EMBODIMENT

Reference will now be made in detail to the present preferred embodiment of the invention, an example of which is illustrated in the accompanying drawings.

Figure 1:
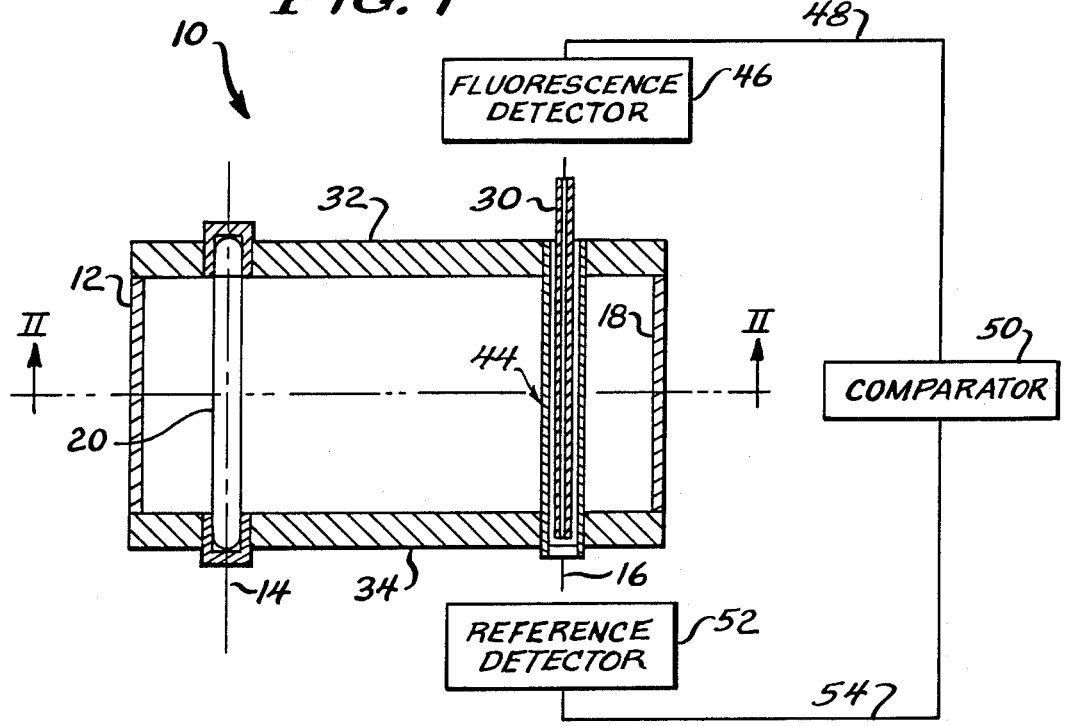
FIG. 1 is a block schematic diagram of a first preferred embodiment of an ellipsoidal cylinder fluorescence analyzer in accordance with the present invention.

A preferred embodiment of an ellipsoidal cylinder fluorescence analyzer in accordance with the present invention is shown in FIGS. 1 and 2 and is represented generally by the numeral 10. The fluorescence analyzer 10 includes an ellipsoidal cylinder having a first focal line a second focal line and an internal reflective surface. As embodied herein, the ellipsoidal cylinder 12 has a first focal line 14, a second focal line 16, and an internal wall 18 that is made highly reflective through conventional means. Ellipsoidal cylinder 12 can be of any material, such as metal or plastic, provided that its generally ellipsoidal shape can be initially fabricated and maintained and that internal wall 18 is made of a material that is inherently reflective or can be coated, treated or otherwise made reflective.

In accordance with the present invention a radiation source is disposed substantially along the first focal line of ellipsoidal cylinder 12. As embodied herein radiation source 20 is disposed substantially along first focal line 14 of ellipsoidal cylinder 12. Radiation source 20 is, as embodied herein, a multi-wavelength energy source such as a xenon flashtube.

Figure 3:
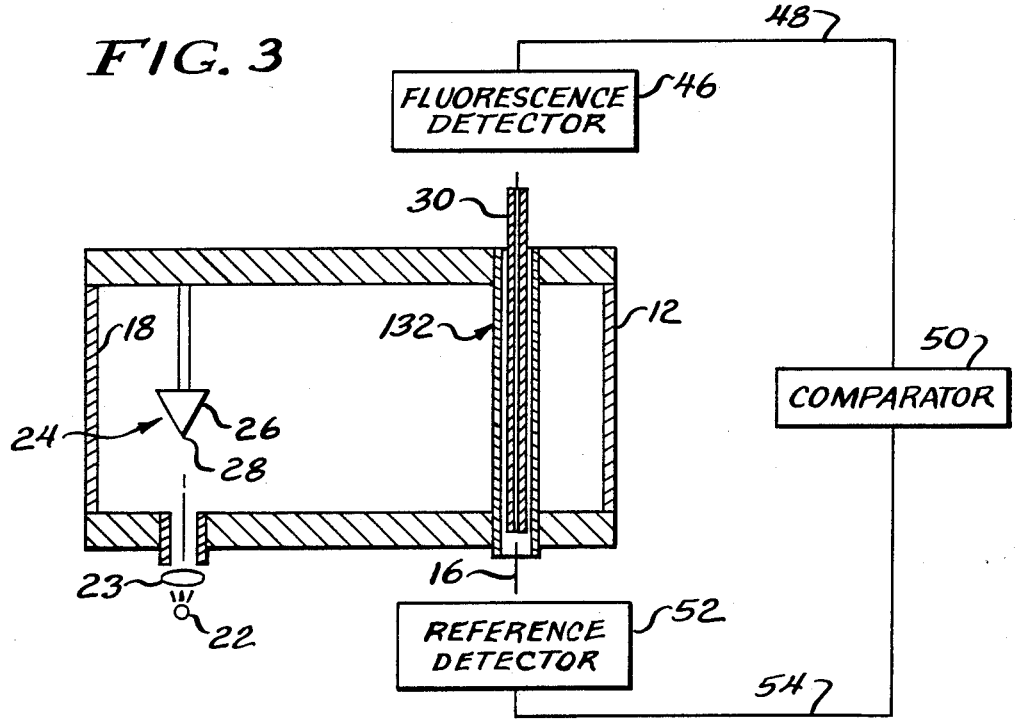
FIG. 3 is a block-schematic diagram of a second preferred embodiment of an ellipsoidal cylinder fluorescence analyzer in accordance with the present invention.

Also as embodied herein, and shown in FIG. 3, the radiation source may be a laser source 22 with appropriate collimating means, such as a collimating lens 23, in combination with a conical reflector 24 that has a reflective surface 26. Conical reflector 24 is disposed within the cavity of ellipsoidal cylinder 12 and its symmetric axis of rotation is coincident with first focal line 14 of ellipsodal cylinder 12. The apex 28 of conical reflector 24 is directed towards point source 22 and surface 26 of conical reflector 24 is reflective. Radiation emanating from laser source 22 is reflected from surface 26 of conical reflector 24 towards internal wall 18 of ellipsoidal cylinder 12. Internal wall 18 of the ellipsoidal cylinder is made reflecting so that the radiation reflected from surface 26 of conical reflector 24 is directed toward second focal line 16 of elliposidal cylinder 12.

For a more complete description of the above-described laser source and conical reflector, and the manner in which the components are used in combination with an ellipsoidal cylinder to produce illumination at on of its focal lines, attention is invited to U.S. Pat. No. 4,672,169 granted June 9, 1987 which is hereby specifically incorporated by reference.

Also in accordance with the present invention a container suitable for containing the sample is disposed substantially along the second focal line of the ellipsoidal cylinder. As embodied herein, and as shown in FIGS. 1 and 2, the sample container is a discrete capillary tube 30 and is located so that its centerline is substantially coincident with, or along, the second focal line 16. Discrete capillary tube 30 contains a sample, not shown in the drawing, that is to be analyzed using the apparatus and method of the present invention. It should be understood that while the sample container in accordance with the present invention is shown in FIGS. 1, 2 and 3 and described as being a discrete capillary tube 30, the present invention encompasses non-capillary tubes such tubing non-capillary dimensions or pipes.

As shown in FIG. 1, a top cavity plate 32 and a bottom cavity plate 34 are provided. Cavity plates 32 and 34 establish a closed volume, light tight seal to prevent the passage of radiation into the cavity established by ellipsoidal cylinder 12. In addition, cavity plates 32 and 34 establish and hold the relative positions of the optical components in the ellipsoidal cylinder such as the sample container, filter means and the radiation source.

Figure 4:
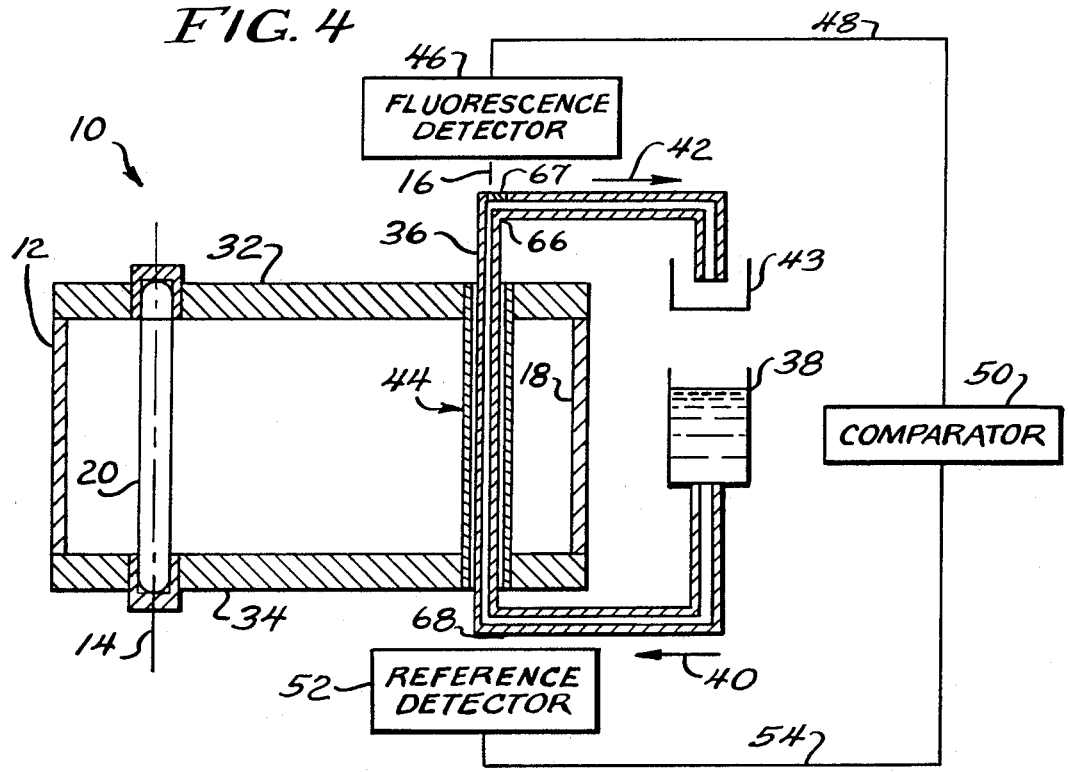
FIG. 4 is a block schematic diagram of a third preferred embodiment of an ellipsoidal cylinder fluoresence analyze in accordance with the present invention.

FIG. 4 is a third preferred embodiment of an ellipsoidal fluoresence analyzer in accordance with the present invention. As embodied herein, the sample container is a flow cell 36. Flow cell 36 is a capillary tube that defines a loop from a sample supply means 38 to the ellipsoidal cylinder 12 and to the waste means 43. That portion of the flow cell 36 that lies along the second focal line 16 of the ellipsoidal cylinder 12 is the sample container. Sample from the sample supply means 38 is made to flow through flow cell 36 from the sample supply means 38, as indicated by arrow 40, through flow cell 36 and along a path indicated by arrow 42 to a waste means 43. In this way the fluoresence properties of a sample can be continuously monitored as it flows through the flow cell 36. In addition, a stopped flow analysis can be made when the flow of sample through the flow cell is stopped.

In accordance with the present invention, filter means are disposed between the radiation souce and the sample container for passing a selected portion of the electromagnetic spectrum. As embodied herein, the filter means is a cylindrical interference filter 44 as shown in FIGS. 1 and 2. Cylindrical filter 44 acts as an interference filter that allows only monochromatic radiation to pass through it. The monochromatic radiation that passes through the cylindrical interference filter 44 is the excitation radiation wavelength that is desired to excite the fluorescent sample contained within capillary tube 30. The radiation of the desired excitation radiation wavelength then passes through the cylindrical filter to fall incident on capillary tube 30 which contains the sample.

In accordance with the present invention the ellipsoidal cylinder fluorescence detector includes fluorescence detector means for detecting fluorescent radiation emanating from the sample container and generating a signal in response thereto. As embodied herein, and as shown in FIGS. 1 and 2, the fluorescent detector comprises a detector 46 adjacent the sample container 30 that is connected through a signal line 48 to comparator means 50. The purpose and operation of the comparator means 50 is more fully explained hereinbelow.

Also in accordance with the present invention, the ellipsoidal cylinder fluorescence detector includes reference detector means for detecting radiation that has passed through the filter means and generating a signal in proportion thereto. As embodied herein the reference detector means includes a detector 52 disposed adjacent the cylindrical filter 44 and connected through a second signal line 54 to the comparator means 50.

Figure 5:
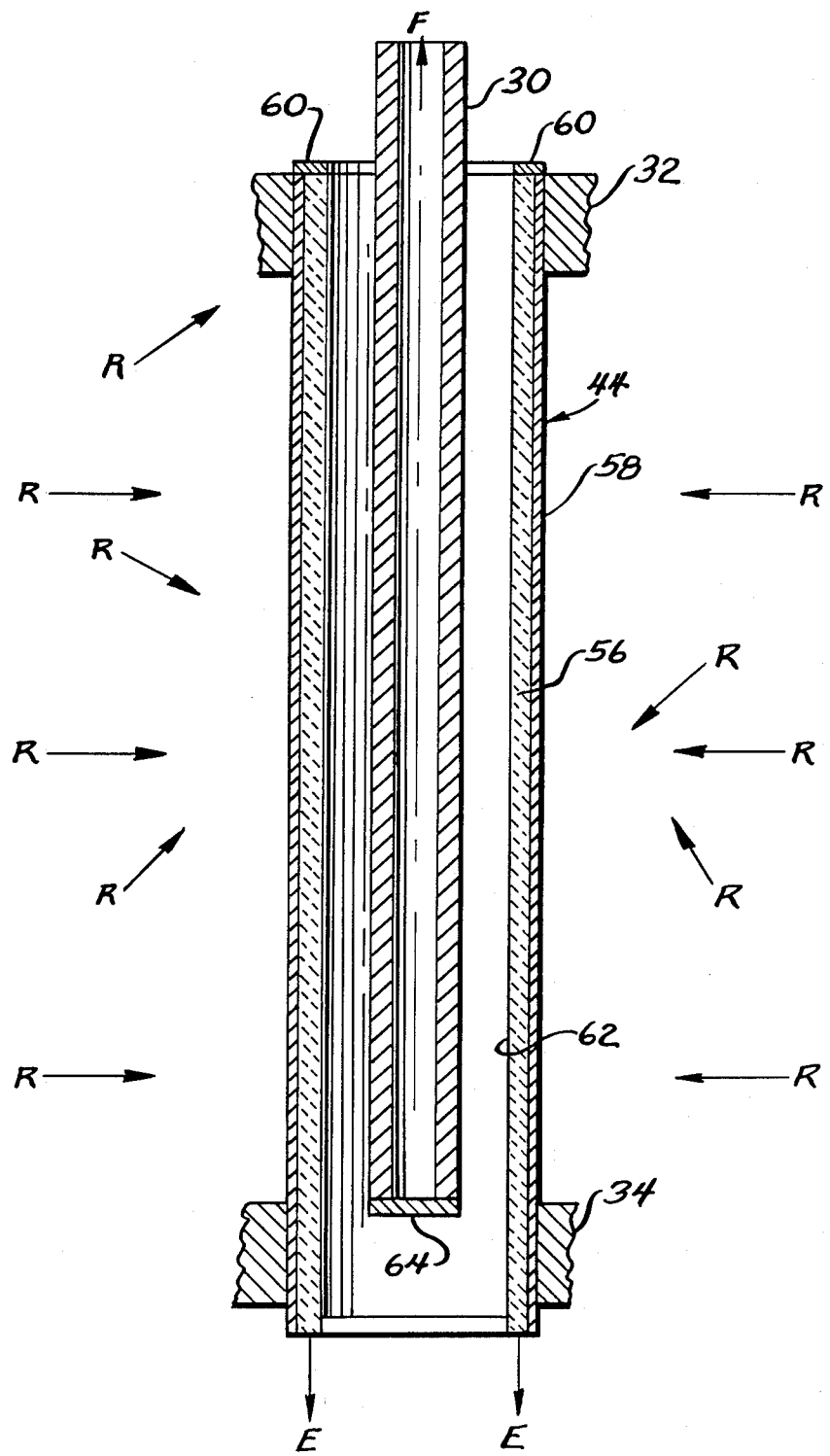
FIG. 5 is a side-sectional view of a cylindrical filter and a capillary tube useful in an ellipsoidal cylinder fluoresence analyzer in accordance with the present invention.

Referring now to FIGS. 1 and 5 it can be understood how the excitation radiation and the fluorescence radiation is delivered to reference detector 52 and fluorescence detector 46, respectfully.

The multi-wavelength energy, designated by R, that emanates from radiation source 20 falls incident on cylindrical filter 44. As shown in FIG. 5, cylindrical filter 44 includes a cylindrical substrate 56 of, for example glass, and a filter sheet 58. The filter sheet 58 is wrapped around substrate 56 and passes only a desired excitation radiation wavelength, E. As indicated by the random pattern of the arrows labeled 'R' in FIG. 5, the source radiation falls on cylindrical filter 44 at a variety of angles of incidence. Accordingly, as is known to those skilled in the art, a portion of the radiation, R, will be reflected by the cylindrical filter 44. Some of the radiation, R, will pass through filter sheet 58 into substrate 56, pass through substrate 56 and fall incident on discrete capillary tube 30. Some of the excitation energy, E, that passes through filter sheet 58 will, however, have an angle of incidence greater than the critical angle for substrate 56. These rays will be internally reflected in substrate 56, propagate along the length of substrate 56 and emerge from substrate 56 as shown by the arrows E. It is these rays of excitation radiation, E, that are detected by reference detector 52 of FIG. 1. Some of the excitation energy E, internally reflected in subsrate 56, will propagate toward the top of substrate 56. This radiation is blocked from exiting from substrate 56 by a top coating 60.

The excitation radiation having an angle of incidence less than the critical angle for substrate 56 does pass through internal wall 62 of substrate 56 to fall incident on capillary tube 30 and pass into discrete capillary tube 30. These rays of excitation radiation excite fluorescent matter entrained in the sample solution that is contained in discrete capillary tube 30. The excited fluorescent matter flouresces thus emanating fluorescent radiation, F. This fluorescent radition F, is blocked from passage out of the bottom of discrete capillary tube 30 by an end cap 64. The fluorescent radiation F, is internally reflected within discrete capillary tube 30, propagates along the length of discrete capillary tube 30 and exits from discrete capillary tube 30 in a direction indicated by the arrow F. The fluorescent radiation F, is thereupon detected by the fluorescence detector 46 shown in FIG. 1.

Referring now to FIG. 4, it can be understood how the excitation radiation is delivered to reference detector 52 and fluoresence detector 46, respectively, when the sample container is a portion of a flow cell rather than the discrete capillary tube 30 of FIG. 1.

The cylindrical filter 44 filters out substantially all radiation except the desired excitation wavelength as described in reference to FIG. 5. Also as described in reference to FIG. 5, the substrate 56, not shown in FIG. 4, directs the excitation radiation, E, to the reference detector 52. The excitation radiation passes through the walls of that portion of the flow cell 36 that lies along the second focal line 16 of the ellipsoidal cylinder 12. The fluorescent radiation generated by the excitation radiation reacting with fluorescent matter propagates within flow cell 36 toward both reference detector 52 and fluoresence detector 46 as shown in FIG. 4. An elbow 66 changes the direction of flow of the the flow cell 36. Accordingly, fluorescent radiation propagating within the flow cell 36 can pass through a window 67 of the elbow 66 to fall incident on the fluorescent radiation detector 46. The window 67 is an integral portion of the elbow that is substantially transparent to the fluorescent radiation. Flourescent radiation propagating along the flow cell 36 in the opposite direction is blocked from the reference detector by, for example, a mask 68.

The comparator means 50, shown in FIG. 1, compares the signal from the reference detector 52 and fluoresence detector 46. Briefly, and is known to those skilled in the art, comparator means 50 receives a signal along line 54 from the reference detector 52 that is indicative of the intensity of the excitation radiation emanating from substrate 56. In addition, comparator means 50 receives a signal from the fluoresence detector 46 along line 48 that is proportional to the fluoresence radiation emanating from the sample contained in capillary tube 30. Both reference detector 52 and fluoresence detector 46 are responsive to the wavelength of excitation or fluoresence radiation, respectively, incident on them. Thus, by comparing the relative outputs from the reference detector 52 and fluoresence detector 46 the presence and concentration of fluoresence material in the sample fluid contained in the capillary tube 30 can be ascertained.

Figure 6:
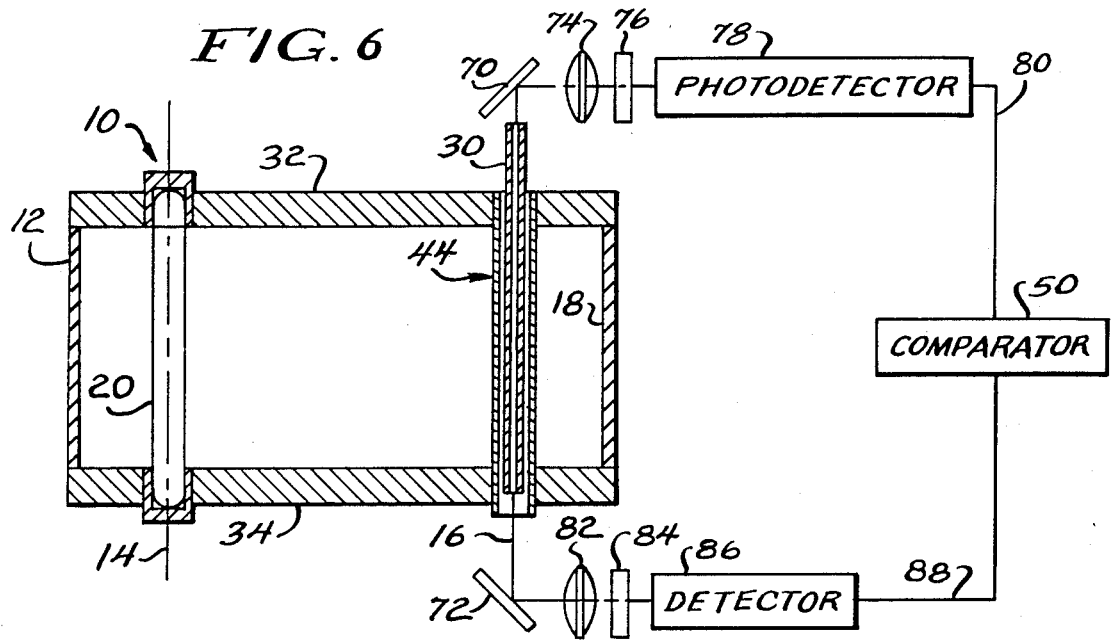
FIG. 6 is a block schematic diagram of a fourth preferred embodiment of an ellipsoidal cylinder fluorescence detector in accordance with the present invention.

FIG. 6 is another preferred embodiment of an ellipsoidal fluorescence detector in accordance with the present invention. Reference numerals used previously in reference to FIGS. 1–5 have the same meanings ascribed to them when used in reference to corresponding items in FIG. 6.

FIG. 6 illustrates the addition of first and second folding mirrors 70 and 72, respectively. First folding mirror 70 directs fluorescent radiation emanating from the capillary tube 30 to an imaging lens 74 that images the fluorescent radiation through a filter 76 on a photodetector 78. The imaging lens 74 ensures an efficient collection of energy emanating from the capillary tube 30 while the filter 76 ensures that only the fluorescent radiation of the wavelength of interest reaches the detector 78. The detector 78 is, in turn, connected to comparing means 50 through a signal line 80.

Second folding mirror 72 directs excitation radiation that emanates from substrate 56 as described in reference to FIG. 5, to an imaging lens 82 that images excitation radiation through a filter 84 to a detector 86. Imaging lens 82 ensures an efficient collection of energy emanating from the substrate 56 while filter 84 ensures that only the excitation radiation of the wavelength of interest reaches detector 86. Detector 86 is connected to comparing means 50 through a signal line 88.

FIGS. 7, 8 and 9 show further embodiments of the filter means in accordance with the present invention.

As embodied in FIG. 7 the filter means is a medial filter 90. Medial filter 90 is disposed within the ellipsoidal cylinder 12 at a point between the radiation source 20 and the capillary tube 30. Medial filter 90 extends vertically and horizontally across the interior of ellipsoidal cylinder 12 to sealingly join the internal wall 18 of the ellipsiodal cylinder and the cavity plates 32 and 34, not shown in FIG. 7. In this way the radiation emanating from radiation source 20 must pass through the medial filter 90 before it reaches the capillary tube 30. As in the case of cylindrical filter 44 of FIGS. 1 and 2, medial filter 90 of FIG. 7 is an interference filter that passes only monochromatic radiation from multiwavelength radiation emitted by radiation source 20.

When the analysis of the sample disposed in the sample container requires it, it is desirous to expose such a sample to more than one excitation wavelength. In such a situation, more than one filter must be employed, each passing a unique wavelength of excitation radiation. FIGS. 8 and 9 illustrate apparatuses for disposing desired ones of a plurality of unique filters between the radiation source and the sample container.

FIG. 8 shows a reciprocating filter holder 92 having two halves 94 and 96. First half 94 has medial filter 90 constrained within it while the second half 96 has a second, different, medial filter 98 constrained within it. Filter holder 92 is joined by a mechanical link 100 to a reciprocating motor 102. Reciprocating motor 102 is connected to a power source, not shown, through a power line 104 and to control means, not shown, through a control line 106. An ellipsoidal cylinder 108 is provided that has first and second slots, 110 and 112, respectively, through which filter holder 92 is free to slide.

In response to a signal from the control means reciprocating motor 102 acts to slide filter holder 92 in the direction of arrow R. This causes first half 94 of filter holder 92 to slide out of the ellipsoidal cylinder 108 through second slot 112 and second half 96 of the filter holder 92 to slide into the ellipsoidal cylinder 108 through the first slot 110. In this way a different filter can be selected, hence a different excitation radiation wavelength can be selected.

A rotating filter device 114 as shown in FIG. 9 acts to dispose any desired one of a plurality of filters in an elliposidal cylinder 116 between radiation source 20 and capillary tube 30. A plurality of filter holders, such as, for example, 120 and 122, are fixed to the circumference of a rotating hub 118. Each of the filter holders 120 and 122 holds a different filter 121 and 123, respectively. Rotating hub 118 is connected through a shaft 124 to a motor 126. In turn, the motor is connected to a power source and control means, not shown, through lines 128 and 130, respectively. The ellipsoidal cylinder 116 includes a slot 132 through the wall thereof to accept the filter holders 120 and 122. The cavity plates 32 and 34, not shown in FIG. 9, have slots corresponding to slot 132 to accomodate the filter holders 120 and 122 as they rotate into or out of the ellipsoidal cylinder 116. In response to a signal from the control means, the motor 126 is actuated to rotate. Filter holder 120 and its associated filter 121 are rotated out of the ellipsoidal cylinder 116 through slot 132 and another filter, such as filter 123 in filter holder 122, is rotated into place through slot 132.

The reference detector 52 is disposed in the ellipsoidal cylinder 12, 108 or 116 of FIGS. 7, 8, and 9, respectively. In each case it is disposed at a location within the ellipsiodal cylinder as to be exposed only to excitation radiation that has passed through the filter means. The fluoresence detector and comparator means and signal processing are the same as described in reference to FIGS. 1 to 4 depending on whether a discrete capillary tube or flow cell, respectively, are used.

In some embodiments of the present invention, such as shown in FIG. 3 and described in reference thereto, a monochromatic source of radiation is used. In such an embodiment the wavelength of the monochromatic source is chosen to be the wavelength of the desired excitation radiation. Accordingly, filter means disposed between the radiation source and the sample container are not required. A cylinder 132 is provided made of, for example, glass to perform the same function as the substrate 56 described in reference to FIGS. 1 and 5. That is, the cylinder 132 guides a portion of the excitation radiation, E, to the reference detector 52. The structure and function of the discrete capillary tube 30, the fluorescence detector 46, the reference detector 52 and the comparator means 50 are as described in reference to FIGS. 1 and 5. Additionally, a flow cell 36, as shown in FIG. 4 and described in reference thereto may be employed in place of the discrete capillary tube 30 of FIG. 3.

It will be apparent to those skilled in the art that various modifications and variations can be made in the ellipsoidal fluorescence detector of the present invention without departing from the scope or spirit of the invention. For example, the discrete capillary tube 30 and the flow cell 36 are illustrated as being cylindrical. It should be understood, however, that these components can have any cross-sectional configuration such as oval, square, or triangular. Thus, it is intended that the present invention cover the modifications and variations of this invention provided they come within the scope of the appended claims and their equivalents.

What is claimed is:

1. An ellipsoidal cylinder fluorescence analyzer for analyzing a sample comprising:

an ellipsoidal cylinder having a first focal line, a second focal line, and an internal reflective surface;

a radiation source disposed substantially along said first focal line;

a container suitable for containing the sample disposed substantially along said second focal line;

filter means disposed inside said ellipsoidal cylinder effective to shield said sample container from all but a selected portion of the radiation emanating from said radiation source, including reflected radiation;

fluorescence detector means for detecting fluorescent radiation emanating from said sample container and generating a signal in response thereto;

reference detector means for detecting radiation that has passed through said filter means and generating a signal in proportion thereto; and comparator means for comparing the signals from said fluorescence and reference detector means.

2. An ellipsoidal cylinder fluorescence analyzer as claimed in claim 1, wherein said sample container comprises a discrete tube.

3. An ellipsoidal cylinder fluorescence analyzer as claimed in claim 1, wherein said sample container comprises a flow cell.

4. An ellipsoidal cylinder fluorescence analyzer as claimed in claim 1, wherein said radiation source comprises a xenon flashtube.

5. An ellipsoidal cylinder fluorescence analyzer as claimed in claim 1, wherein said filter means comprises a cylinder disposed surrounding said sample container.

6. An ellipsoidal cylinder fluorescence analyzer as claimed in claim 1, wherein said filter means is disposed intermediate said first focal line and said second focal line of said ellipsoidal cylinder.

7. An ellipsoidal cylinder fluorescence analyzer as claimed in claim 1, wherein said filter means comprises:

a plurality a filter segments, each capable of passing a selected portion of the electromagnetic spectrum;

means for holding said plurality of filter segments; and moving means for moving said holding means to selectively dispose one or more of said plurality of filter segments between said radiation source and said sample container.

8. An elliptical cylinder fluorescence analyzer as claimed in claim 1, which further includes collection means for collecting fluorescent radiation emanating from said sample container.

9. An elliptical cylinder fluorescence detection system as claimed in claim 2 which further includes:

said filter means being disposed on a cylindrical substrate disposed concentrically about said sample container;

first collection means disposed between one end of said sample container and said fluorescence detector means to collect fluorescence radiation emanating from said sample container and focus a portion of such radiation of said fluorescence detector means; and second collection means disposed between one end of said cylinder substrate and said reference detector means to collect filtered radiation eminating from said cylinder substrate and focusing it on said reference detector means.

10. An elliptical cylinder fluorescence detection system as claimed in claim 3 which further includes:

said filter means being disposed on a cylindrical substrate disposed concentrically about said sample container;

first collection means disposed between one end of said sample container and said fluorescence detector means to collect fluorescence radiation emanating from said sample container and focus a portion of such radiation on said fluorescence detector means; and second collection means disposed between one end of said cylinder substrate and said reference detector means to collect filtered radiation eminating from said cylinder substrate and focusing it on said reference detector means.

11. A method for detecting the fluorescence properties of a sample comprising:

disposing a radiation source substantially on the first focal line of an ellipsoidal cylinder having a reflective internal surface;

disposing a sample container containing such sample on the second focal line of the ellipsoidal cylinder;

shielding said sample container from all but a selected portion of the radiation emanating from said radiation source, including reflected radiation, by means of a filter disposed inside said ellipsoidal cylinder;

energizing the radiation source so that radiation is passed to the sample container and sample;

detecting fluorescent radiation emanating from the sample, and generating a signal in response thereto;

detecting excitation radiation that has passed through the filter means and generating a signal in response thereto; and comparing the fluorescent radiation and excitation radiation signals to determine the presence and concentration of fluorescent material in the sample.

12. A method as claimed in claim 11 further including flowing the sample throughout the container while the steps of energizing, detecting fluorescent radiation, detecting radiation that has passed through the filter means and comparing are performed.

13. An ellipsoidal cylinder fluorescence analyzer for analyzing a sample comprising: an ellipsoidal cylinder having a first focal line, a second focal line, and an internal reflective surface;

a radiation source disposed substantially along said first focal line;

a container suitable for containing the sample disposed substantially along said second focal line;

filter means comprising a cylinder disposed surrounding said sample container for passing a selected portion of the electromagnetic spectrum;

fluorescence detector means for detecting fluorescent radiation emanating from said sample container and generating a signal in respnose thereto;

reference detector means for detecting radiation that has passed through said filter means and generating a signal in proportion thereto; and comparator means for comparing the signals from said fluorescence and reference detector means.

14. An ellipsoidal cylinder flourescence analyzer as claimed in claim 13, wherein said sample container comprises a discrete tube.

15. An ellipsoidal cylinder fluorescence analzyer as claimed in claim 13, wherein said sample container comprises a flow cell.

16. An ellipsoidal cylinder fluorescence analyzer as claimed in claim 13, wherein said radiation source comprises a xenon flashtube.

17. An ellipsoidal cylinder fluorescence analyzer as claimed in claim 13, wherein said filter means comprises a plurality of filter segments, each capable of passing a selected portion of the electromagnetic spectrum.

18. An ellipsoidal cylinder fluorescence analyzer as claimed in claim 13, which further includes collection means for collecting fluorescent radiation emanating from said sample container.

19. An elliptical cylinder fluorescence detection system as claimed in claim 14, which further includes:

said filter means being disposed on a cylinder substrate disposed concentrically about said sample container;

first collection means disposed between one end of said sample container and said fluorescence detector means to collect fluorescence radiation emanating from said sample container and focus a portion of such radiation on said fluorescence detector means; and second collection means disposed between one end of said cylinder substrate and said reference detector means to collect filtered radiation emanating from said cylinder substrate and focusing it on said reference detector means.

20. An elliptical cylinder fluorescence detection system as claimed in claim 15 which further includes:

said filter means being disposed on a cylinder substrate disposed concentrically about said sample container;

first collection means disposed between one end of said sample container and said fluorescence detector means to collect fluorescence radiation emanating from said sample container and focus a portion of such radiation on said fluorescence detector means; and second collection means disposed between one end of said cylinder substrate and said reference detector means to collect filtered radiation emanating from said cylinder substrate and focusing it on said reference detector means.

21. A method for detecting the fluorescence properties of a sample comprising:

disposing a radiation source substantially on the first focal line of an ellipsoidal cylinder having a reflective internal surface;

disposing a sample container containing such sample on the second focal line of the ellipsoidal cylinder;

disposing cylindrical filter means substantially coaxially with and around said sample container;

energizing the radiation source so that radiation is passed to the sample container and sample;

detecting fluorescent radiation emanating from the sample, and generating a signal in response thereof;

detecting excitation radiation that has passed through the filter means and generating a signal in response thereto; and comparing the fluorescent radiation and excitation radiation signals to determine the presence and concentration of fluorescent material in the sample.

22. A method as claimed in claim 21 further including flowing the sample throughout the container while the steps of energizing, detecting fluorescent radiation, detecting radiation that has passed through filter means and comparing are performed.

* * * * *